United States Patent [19]
Bisaccia et al.

[11] Patent Number: 5,284,869
[45] Date of Patent: Feb. 8, 1994

[54] PHOTOPHORESIS METHODS FOR TREATING ATHEROSCLEROSIS AND FOR PREVENTING RESTENOSIS FOLLOWING ANGIOPLASTY

[76] Inventors: Emil Bisaccia, 4 Sunnybrook Rd., Basking Ridge, N.J. 07920; Albert S. Klainer, 315 W. 70th St., New York, N.Y. 10023

[21] Appl. No.: 809,590

[22] Filed: Dec. 17, 1991

[51] Int. Cl.$^5$ .................. A01N 43/16; A61K 31/35
[52] U.S. Cl. .................................... 514/455
[58] Field of Search ........................... 514/455

[56] References Cited

U.S. PATENT DOCUMENTS

| | | | |
|---|---|---|---|
| 4,321,919 | 3/1982 | Edelson | 604/28 |
| 4,683,889 | 8/1987 | Edelson | 600/3 |
| 5,116,864 | 5/1992 | March et al. | 514/455 |

Primary Examiner—Nathan M. Nutter
Attorney, Agent, or Firm—Mark E. Waddell

[57] ABSTRACT

The occurence of restenosis following percutaneous transluminal coronary angioplasty is prevented or inhibited using a photopheresis treatment method. In accordance with the photopheresis treatment method, a photoactive compound such as 8-methoxypsoralen is administered to the patient's blood or affected tissue, or some fraction thereof, in vitro or in vivo using conventional administration routes. A portion of the patient's blood or affected tissue is then treated (preferably, extracorporeally) using photopheresis, which comprises subjecting the blood or affected tissue to electromagnetic radiation in a wavelength suitable for activating the photoactive compound, such as ultraviolet light, preferably long wavelength ultraviolet light in the wavelength range of 320 to 400 nm, commonly called UVA light. The treated blood or affected tissue, or a fraction thereof, is returned to the patient (in the case of extracoporeal photopheresis) or remains in the patient (following in vivo photopheresis).

5 Claims, No Drawings

PHOTOPHORESIS METHODS FOR TREATING ATHEROSCLEROSIS AND FOR PREVENTING RESTENOSIS FOLLOWING ANGIOPLASTY

FIELD OF THE INVENTION

The present invention relates to photopheresis methods for treating arteriosclerosis and atherosclerosis. These methods are also particularly useful for the inhibition of restenosis following angioplasty.

BACKGROUND OF THE INVENTION

Fanelli, et al., "Restenosis Following Coronary Angioplasty," American Heart Journal, 119, 357-368 (1990), provides a comprehensive review of restenosis after percutaneous transluminal coronary angioplasty (PTCA), including (i) the mechanisms of angioplasty and restenosis, (ii) clinical aspects of restenosis, (iii) therapeutic trials aimed at decreasing the incidence of restenosis, (iv) management of patients with restenosis and (v) potential future technologies. As reported by Fanelli, et al., the use of PTCA has grown tremendously from a level of approximately 39,000 procedures in 1983 to a number that could exceed 500,000 per year over the next 5 years. Yet despite the tremendous growth and success of PTCA, restenosis remains a major problem, with an overall incidence of 25% to 35%.

Various pharmacologic approaches to prevent restenosis have been tried but, to date, none of them has been demonstrated to significantly alter the rate of restenosis. This has led investigators to attempt non-pharmacological approaches (e.g., intravascular stents, laser ballon angioplasty, etc.). These attempts at preventing restenosis have likewise proved unsuccessful according to Fanelli, et al.

In view of the above there exists a long felt but unsolved need for a technique to prevent or at least inhibit restenosis following percutaneous transluminal coronary angioplasty.

BRIEF DESCRIPTION OF THE INVENTION

In accordance with the present invention a method has been found for treating patients following PTCA to prevent or at least inhibit restenosis using a photoactive compound that binds to nucleic acid upon activation by exposure to electromagnetic radiation of a prescribed spectrum, such as ultraviolet light. Psoralen compounds are particularly preferred for this purpose, especially the compound 8-methoxypsoralen—in which case UVA radiation is preferred for activating said compound.

In accordance with the invention, a photoactive compound such as 8-methoxypsoralen is administered to the patient's blood or angioplasty affected tissue, or some fraction thereof, in vitro or in vivo using conventional administration routes. A portion of the patient's blood or affected tissue is then treated (preferably, extracorporeally) using photopheresis, which comprises subjecting the blood or affected tissue to electromagnetic radiation in a wavelength suitable for activating the photoactive compound, such as ultraviolet light, preferably long wavelength ultraviolet light in the wavelength range of 320 to 400 nm, commonly called UVA light. The treated blood or affected tissue, or a fraction thereof, is returned to the patient (in the case of extracorporeal photopheresis) or remains in the patient (following in vivo photopheresis).

DETAILED DESCRIPTION OF THE INVENTION

According to the claimed methods, a photoactive compound is first administered to the blood or affected tissue of a patient following PTCA. The photoactive compound may be administered in vivo (e.g. orally, intravenously or intracather) or may be administered in vitro to a portion of the patient's blood which has been removed from the patient by employing conventional blood withdrawal techniques. Psoralen compounds are particularly preferred for this purpose, especially the compound 8-methoxypsoralen—in which case UVA radiation is preferred for activating said compound.

Next, the portion of the patient's blood or affected tissue, to which the photoactive compound has been administered is treated by subjecting the portion of the blood or affected tissue to photopheresis using said electromagnetic radiation—for example, ultraviolet light. The photopheresis step is preferably carried out in vitro using an extracorporeal photopheresis apparatus.

The photopheresis step in accordance with the present invention may also be carried out in vivo by irradiating the patient in a photopheresis chamber such as is known in the art for the treatment of psoriasis (PUVA therapy).

A presently preferred extracorporeal photopheresis apparatus for use in the methods according to the invention is currently manufactured by Therakos, Inc., Westchester, Pa. under the name UVAR. A description of the Therakos UVAR photopheresis apparatus may be found in U.S. Pat. No. 4,683,889, granted to R. L. Edelson on Aug. 14, 1987, the contents of which are hereby incorporated by reference in their entirety.

The apparatus includes a pump for removing blood from the patient via a donor needle placed in an appropriate vein of the patient; an irradiation chamber; a radiation source in close proximity to the irradiation chamber and a centrifuge, preferably of the continuous type. The various parts of the apparatus, such as tubing collection bags for the blood and the like, which come in contact with the patient's blood or some fraction thereof, are preferably replaceable so that they may be disposed of after each use to prevent the possibility of transmitting blood-borne infections from one patient to others who are subsequently treated with the apparatus.

The exposure of blood or affected tissue to ultraviolet light in a photopheresis apparatus is within the ability of persons having ordinary skill in the art.

When the photopheresis step is carried out in vitro, at least a fraction of the treated blood or affected tissue is returned to the patient following the photopheresis treatment. Preferably, the treatment method described hereinabove is repeated at an interval of about once per week to about once every four weeks. Most preferably the treatment methods described herein are administered on two successive days and repeated approximately once per month (i.e., the patient preferably receives two treatments every month).

In the case when it is desired to prevent restenosis, the photopheresis treatment described herein is most preferably administered the day following angioplasty, repeated the next day and this two-day treatment is repeated on monthly intervals for a total of five two day treatments over a five month period following angioplasty to prevent or inhibit restenosis.

In view of the disclosure contained herein, those persons who are skilled in the art will be able to adjust the treatment parameters—i.e., dosage of the photoactive compound and electromagnetic radiation, periodicity of treatment (e.g., monthly, weekly, etc.) and the number of treatments administered in each period (e.g., twice per month on two successive days)—depending on the condition of the patient and the patient's response to the treatment.

Preferred photoactive compounds for use in accordance with the present invention are compounds known as psoralens (or furocoumarins) which are described in U.S. Pat. No. 4,321,919 the disclosure of which is incorporated herein by reference in their entirety.

The preferred photoactive compounds for use in accordance with the present invention include the following:
psoralen;
8-methoxypsoralen;
4,5′8-trimethylpsoralen;
5-methoxypsoralen;
4-methylpsoralen;
4,4-dimethylpsoralen;
4,5′-dimethylpsoralen; and
4′,8-methoxypsoralen, The most particularly preferred photoactive compound for use in accordance with the invention is 8-methoxypsoralen.

The determination of an effective dosage of the psoralen compound is within the ability of persons having ordinary skill in the art.

The photoactive compound, when administered to the patient's blood or affected tissue in vivo is preferably administered orally, but also can be administered intravenously, intracatheter and/or by other conventional administration routes.

The preferred dosage of the photoactive compound is in the range of about 0.3 to about 0.7 mg/kg of body weight although larger or smaller doses may be employed. When the photoactive compound is administered in vitro to only a portion of the patient's blood or fraction thereof, it is within the ability of those skilled in the art to calculate a dosage which is equivalent to said range based upon the volume of treated blood or fraction thereof.

When administered orally, the photoactive compound should preferably be administered at least about one hour prior to the photopheresis treatment and no more than about three hours prior to the photopheresis treatment. The timing of administration may be adjusted up or down as needed depending on the bioavailability of the photoactive compound, its expected half-life, etc. If administered intravenously or intracatheter, the times would generally be shorter.

The photopheresis treatment in the treatment methods according to the invention is preferably carried out using long wavelength ultraviolet light (UVA) at a wavelength within the range of 320 to 400 nm. The exposure to ultraviolet light during the photopheresis treatment preferably has a duration of about three to four hours, although shorter or longer treatment periods may be used if desired. The selection of an appropriate wavelength for photopheresis as well as the exposure, depending upon the photoactive compound being employed and the conditions of treatment (e.g., in vivo exposure or in vitro exposure), is within the ability of those skilled in the art in view of the present disclosure.

When the photoactive compound is 8-methoxypsoralen, it is preferred in accordance with the invention to utilize an exposure to UVA radiation of about 2 Joules/meter$^2$ based upon the surface area of the cells in the blood or affected tissue fraction undergoing treatment.

When the photopheresis treatment according to the invention is carried out in vivo, careful attention should be paid to controlling the maximum radiant exposure so as to avoid unnecessary injury to the patient. Methods for calculating maximum radiant exposure to ultraviolet light are known in the art and, therefore, shall not be described herein.

While the inventors do not intend their invention to be limited by a specific theory of operation, it is believed that the described treatment methods act by modifying the patient's immune response to percutaneous transluminal angioplasty. The treatment methods thus are believed to redirect or attenuate physiological response to damage caused by angioplasty that could otherwise result in restenosis. The above-described photopheresis methods may also be used to treat arteriosclerosis and atherosclerosis as a substitute for PTCA.

We claim:

1. A method for inhibiting the occurrence of restenosis following percutaneous transluminal angioplasty in a human patient, said method comprising:
   a. administering to at least a portion of the patient's blood a psoralen compound which becomes activated when exposed to electromagnetic radiation of a prescribed activating spectrum, said psoralen compound being administered in an amount which is sufficient to obtain serum levels which are effective for inhibiting restenosis following percutaneous transluminal angioplasty;
   b. activating the psoralen compound in vitro; and
   c. presenting the resulting treated portion of the patient's blood to the patient's immune system to beneficially alter the patient's response to percutaneous transluminal angioplasty.

2. The method of claim 1, wherein the psoralen compound is selected from the group consisting of psoralen, 8-methoxypsoralen, 4,5′8-trimethylpsoralen, 5-methoxypsoralen, 4-methylpsoralen, 4,4-dimethylpsoralen, 4–5′-dimethylpsoralen, and 4′,8-methoxypsoralen.

3. The method of claim 2, wherein the psoralen compound is 8-methoxypsoralen.

4. The method of claim 3, wherein the dosage of 8-methoxy psoralen is in the range of about 0.3 to 0.7 mg/kg of body weight of the patient.

5. The method of claim 4, wherein steps a–c are carried out on two successive days repeated as needed to maintain inhibition of restenosis.

* * * * *